United States Patent
Ahn

[11] Patent Number: 5,843,170
[45] Date of Patent: *Dec. 1, 1998

[54] APPARATUS AND METHOD FOR PERFORMING ANEURYSM REPAIR

[76] Inventor: Sam Seunghae Ahn, 100 UCLA Medical Plaza, Suite 510, Los Angeles, Calif. 90024

[*] Notice: The term of this patent shall not extend beyond the expiration date of Pat. No. 5,527,355.

[21] Appl. No.: 842,336

[22] Filed: Apr. 24, 1997

Related U.S. Application Data

[60] Division of Ser. No. 635,641, Apr. 22, 1996, abandoned, which is a continuation-in-part of Ser. No. 300,059, Sep. 2, 1994, Pat. No. 5,527,355.

[51] Int. Cl.⁶ ...................................................... A61F 2/06
[52] U.S. Cl. ................................................................ 623/1
[58] Field of Search ............................................ 623/1, 12

[56] References Cited

U.S. PATENT DOCUMENTS

| | | | |
|---|---|---|---|
| 3,435,823 | 4/1969 | Edwards | 606/153 |
| 3,726,279 | 4/1973 | Barefoot et al. | 606/151 |
| 3,789,828 | 2/1974 | Schulte | 623/66 |
| 4,140,126 | 2/1979 | Choudhury | 128/325 |
| 4,190,909 | 3/1980 | Ablaza | 623/1 |
| 4,787,899 | 11/1988 | Lazarus | 623/1 |
| 5,084,065 | 1/1992 | Weldon et al. | 623/1 |
| 5,104,399 | 4/1992 | Lazarus | 623/1 |
| 5,219,355 | 6/1993 | Parodi et al. | 606/191 |
| 5,246,456 | 9/1993 | Wilkinson | 623/12 |
| 5,330,490 | 7/1994 | Wilk et al. | 606/153 |
| 5,456,246 | 10/1995 | Schmieding et al. | 600/201 |
| 5,527,355 | 6/1996 | Ahn | 623/1 |

FOREIGN PATENT DOCUMENTS

| | | | |
|---|---|---|---|
| 617930 | 10/1994 | European Pat. Off. | 623/1 |
| 2269104 | 2/1994 | United Kingdom | 623/1 |

*Primary Examiner*—Michael J. Milano
*Attorney, Agent, or Firm*—Blakely, Sokoloff, Taylor & Zafman LLP

[57] ABSTRACT

An apparatus and method of treating an aneurysm by applying to an aneurysmal blood vessel a band around its exterior surface, at the position where the attachment system of the graft attaches the graft to the vessel. The band can be in the form of a strap with an attachment means such a Velcro®, or a clasp, or it can be heat sealed onto the vessel or sewn thereon. The band can also be in the form of a support strap with a cable-tie buckle on one end and protruding ridges on the other end, wherein the support strap contains a plurality of protruding nodules along its length on the side of the support strap that contacts the blood vessel and a channel along its length on the side of the support strap that contacts the blood vessel for those applications wherein the graft retention system contains barbs or stables that penetrate the blood vessel wall.

6 Claims, 10 Drawing Sheets

APPARATUS AND METHOD FOR PERFORMING ANEURYSM REPAIR

BACKGROUND OF THE INVENTION

1. Related Application

This is a divisional of application Ser. No. 08/635,641 filed Apr. 22, 1996, now abandoned, which is a continuation-in-part of application Ser. No. 08/300,059 filed Sep. 2, 1994, now U.S. Pat. No. 5,527,355.

2. Field of the Invention

This invention relates to the field of vascular surgery, and more specifically, is directed to an apparatus and method for repairing a vascular aneurysm.

3. Art Background

The prior art method of treating a vascular aneurysm and some other vascular problems has been to excise the aneurysmal tissue and replace it with a synthetic graft or a graft from another section of the body. This surgery has been extremely risky, and a high mortality rate has been observed, primarily because the condition of the patients undergoing the surgery is generally weak.

In recent years, a number of companies have devised new methods and devices for treating aneurysms and other vascular disease in which the blood vessels are damaged and unable to safely retain the blood passing therethrough. The devices are comprised of vascular prosthetic graft with a connecting means of some type for connecting the prosthesis to the damaged blood vessel at a position displaced from the aneurysm or damage, the prosthesis being sized to fit within the blood vessel, so that the graft permits the blood to travel through the damaged vessel without applying any pressure to the damaged vessel at the point of damage.

U.S. Pat. No. 4,140,126 discloses one such prior art device and method for repairing an aneurysm. This device is positioned in a vessel in a collapsed form, and is then expanded and then attached to the inside of the wall of the vessel with hooks which extend when the device is expanded from its collapsed form.

U.S. Pat. No. 4,787,899 discloses an artificial intraluminal graft with u-shaped staples near the end for securing the graft to the vessel. U.S. Pat. No. 5,104,399, which is a continuation in part of the '899 patent, discloses a generally cylindrical graft with a staple assembly in a v-shaped lattice work which is assembled into its operational configuration by the inflation of a balloon in the interior of the assembly.

U.S. Pat. No. 5,219,355 discloses an intraluminal prosthesis for repairing aneurysms which utilizes a catheter having two inflatable balloons, one near each end of the prosthesis, for securing the prosthesis in place in the vessel.

While the retention systems appear to be effective in retaining the grafts in the vessel, over time, it is anticipated, and there have been some recent reports that the vessel wall where the graft connects thereto becomes weakened, and a subsequent aneurysm may occur at that position. As an additional factor, the penetration into the wall by the staples causes some fibrosis, and the tissue buildup at the location of the connection can cause some blood flow restriction which would increase the pressure on the vessel walls at the site of contact between the blood vessel and the graft. This condition may also increase the risk of a subsequent aneurysm.

The present invention is designed to operate in conjunction with a number of various retention systems for retaining a vascular graft in a vessel by attaching the graft to the interior wall of the vessel, without the risk. Each of these has certain deficiencies which are described below, which deficiencies are resolved by the present invention.

SUMMARY OF THE INVENTION

A method and apparatus are disclosed which overcome the disadvantages and limitations associated with the prior art devices, and which can be used in conjunction with the prior art system to ensure that the vessel retention system of a vascular graft functions without causing certain complications. More specifically, the complications, which may occur over time, relate to a weakening of the wall of the blood vessel at the attachment site of the graft to the vessel, causing an aneurysm at the new location, typically upstream, but possibly downstream from the original aneurysmal site. The secondary aneurysm is the result of the weakening of the wall of the blood vessel due to the use of staples to attach the graft to the vessel, and various other factors.

The present invention is an apparatus and method of alleviating this problem by applying to the blood vessel a band around its exterior surface, at the position where the attachment system of the graft attaches the graft to the vessel. The band can be in the form of a strap with an attachment means such as Velcro®, or a clasp, or it can be heat sealed onto the vessel or sewn thereon. The band can be applied laparoscopically or using direct field of vision prior to, during, or after placement of the intraluminal graft. Typically in the application of the graft it is inserted in the blood vessel downstream from the aneurysm and then advanced to the site of the aneurysm through the interior of the vessel, and then expanded into its full radial size and secured in place using the retention system designed for it, of the different systems known in the art. The position of the graft can be confirmed using x-ray or other imaging technique. Once the graft is placed, assembled and secured in place with its retention system, the band can be applied to the exterior of the blood vessel, or the band can be applied first and the graft then positioned to fit the band. The length of the band can vary, but should be at least long enough to envelope the entire length of the blood vessel to which the graft is attached at the attachment site.

In a particular embodiment of the invention, the band is in the form of a support strap with a cable-tie buckle on one end and protruding ridges on the other end. The support strap is secured around the blood vessel by forcibly inserting the end of the strap with the protruding ridges through the cable-tie buckle and using the force of the ridges against the cable-tie buckle to hold the strap in place.

In another embodiment, the band is a support strap wherein the support strap contains a plurality of teeth along its length on the side of the support strap that contacts the blood vessel. The teeth serve to grip the blood vessel and reduce slippage of the support strap.

In a further embodiment, the band is a support strap wherein the support strap contains a channel along its length on the side of the support strap that contacts the blood vessel. The channel is particularly useful for those applications wherein the graft retention system contains barbs or staples that penetrate the blood vessel wall. The exposed portion of the barbs or staples on the outside of the blood vessel penetrate into the channel of the strap. The channel of the strap may be covered with a penetrable support membrane that the exposed barbs or staples may further penetrate to enter the channel. Finally, the channel may be marked to permit the surgeon to align the exposed portion of the barbs or staples in the channel.

BRIEF DESCRIPTION OF THE DRAWINGS

The objects of the present invention will be described with respect to the following figures in which.

DETAILED DESCRIPTION OF THE INVENTION

An apparatus is described for securing on a blood vessel a vascular graft containing a retention system. A method of securing the vascular graft is also described. Renal arteries extend from the abdominal aorta and the arteries are divided into the common iliac artery at the lower most end. The aorta is a major blood vessel of the body and is characterized by generally healthy tissue. However, one section of the aorta is damaged, and this is where a large aneurysm has formed characterized by a bulge in the wall of the aorta. If the aneurysm is not repaired or otherwise treated in time it will eventually rupture causing a fatal hemorrhage within a short period of time. It will be understood by persons of skill in the art that while the present invention is described with reference to an aneurysm in the aorta, the present invention will be useful in the treatment of aneurysm in other vessels as well, the usefulness of the vascular graft technology in the repair of aneurysm being generally known in the art.

The present invention is an adjunct to a prosthetic graft for repairing the damaged blood vessel. The prosthetic graft is primarily made of generally biologically acceptable material, such as Dacron, Nylon, Gortex, and the like. The graft is an elongated tube of the material and a retention systems for retaining the graft within the blood vessel. The retention system is expandable and collapsible, which is presently necessary and consistent with the method of implantation in which the graft is installed in a blood vessel at a site remote from the aneurysm, and is then pushed and guided up to the aneurysmal site, and then installed in place in the blood vessel. The retention system is comprised of a cylindrical array of staples which have outward protruding barbs; however, the invention may be utilized with other types of retention systems as well.

Figure 1:
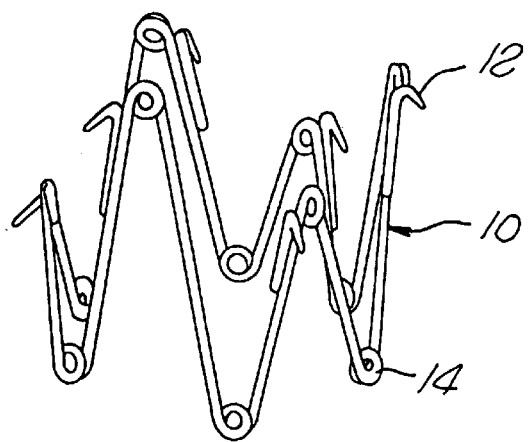
FIG. 1 is an illustration of one type of prior art graft retention system.
Figure 2:
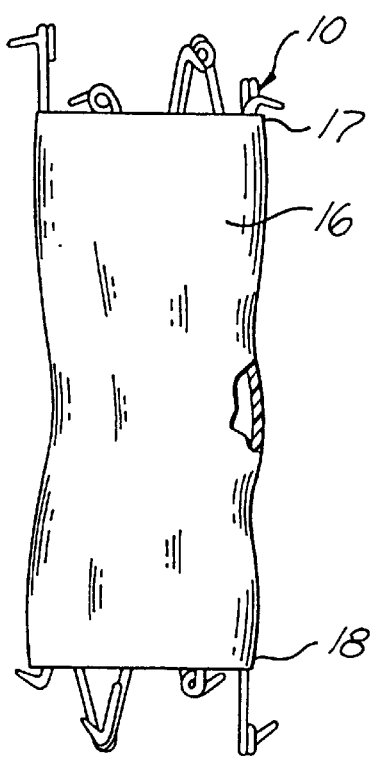
FIG. 2 is a partially cutaway view of a prior art graft with a retention system.

FIG. 1 is an illustration of one prior art graft retention system in which the staples are collapsible and expandable. The graft retention system 10 comprises a plurality of staples or barbs 12 extending outward, and connected together in a v-shaped network with a spring hinge 14 interconnecting each staple. It will be appreciated by persons of skill in the art that there are a number of different graft retention systems, including a variety of different staple configurations and balloon retention systems, and the present invention will work with any of these systems. As shown in FIG. 2, the graft retention system of FIG. 1 is disposed within the vascular graft 16, shown in a partially cutaway view, with the retention system 10 being partially viewable above and below the edges 17 and 18 of the graft.

The graft retention system 10 is retained in the graft by any suitable means.

Figure 3:
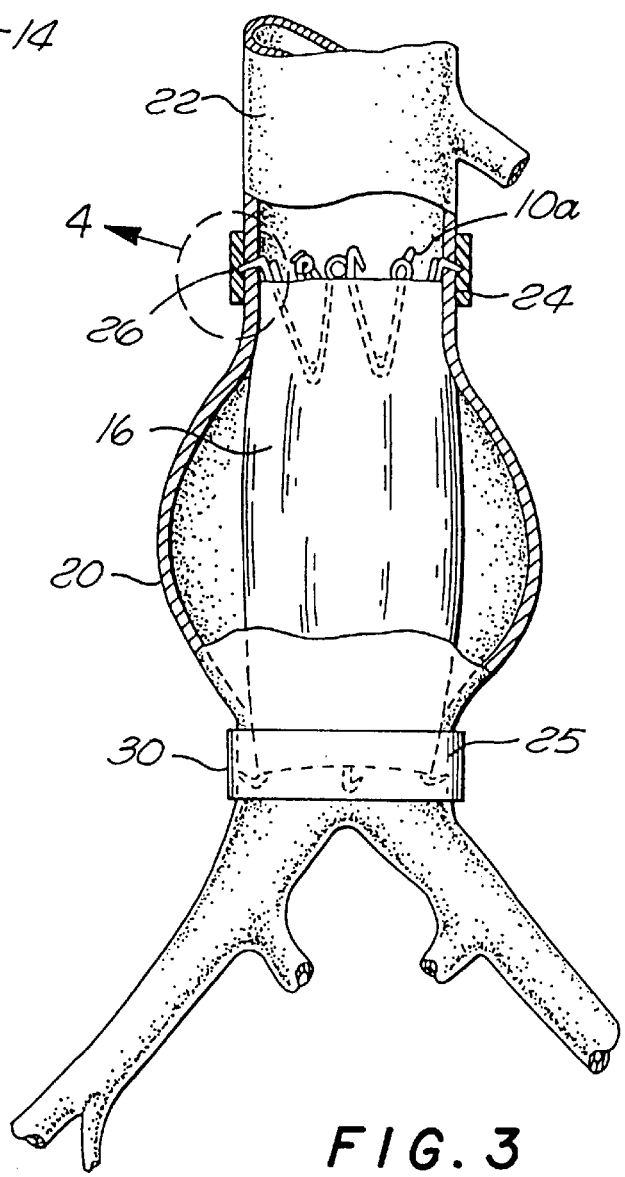
FIG. 3 is a partial sectional view of an aneurysmal blood vessel with a vascular graft disposed therein, and the band of the present invention disposed around the blood vessel at the site where the retention system engages the blood vessel.

FIG. 3 illustrates the present invention which is a band disposed around the exterior of the blood vessel at the location where the retention system is connected to the blood vessel remote from the actual position of the aneurysm. More specifically, the graft 16 is disposed at the site of the aneurysm 20 in the aorta 22. FIG. 3 is a partially cutaway sectional view of the invention disposed in place on the aorta 22 showing that at one end 24, the retention system 10a, shown partially in ghost lines, retains the graft 16 in the aorta 22, and the band 26 of the present invention, shown in sectional view, is disposed around the exterior of the aorta 22 at the location where the retention system 10a joins the graft 16 to the interior of the aorta 22. As a result of the positioning of the band 26, the aorta is supported and the graft 16 is secured in position. At the other end 25 of the graft 16, a second band 30 is shown in full form with the underlying retention system and graft shown in ghost lines. As can be seen, the band is sufficiently wide to carefully overlie the site where the retention system connects to the aorta, but not so wide as to restrict the natural motion of the blood vessel in operation. It will also be appreciated by persons of skill in the art that the band can be of any width which will accomplish the intended purpose of supporting the blood vessel at the site of the connection between the graft and the blood vessel.

Figure 4:
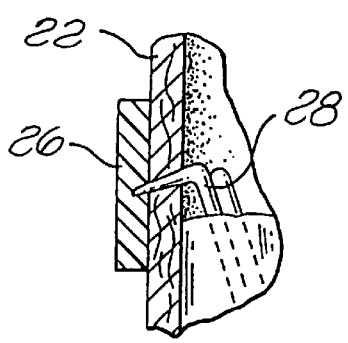
FIG. 4 is an enlarged view of a portion of the present invention disposed on a blood vessel with a retention system, taken through the section designated by the numeral 4 in FIG. 3.

FIG. 4 shows an enlarged view of the present invention strap 26 installed on a blood vessel 22 with a retention system 10a holding the graft 16 to the interior wall of the vessel 22. It will be appreciated that although in the present invention, the barb 28 is disposed entirely through the wall of the vessel 22, the barb 28 does not have to extend all the way therethrough in order for the present invention to function properly. While not being bound to any particular theory, the present invention functions by supporting the blood vessel and preventing it from expanding beyond its natural amount of expansion. It works like a girdle to provide the required support.

Figure 5:
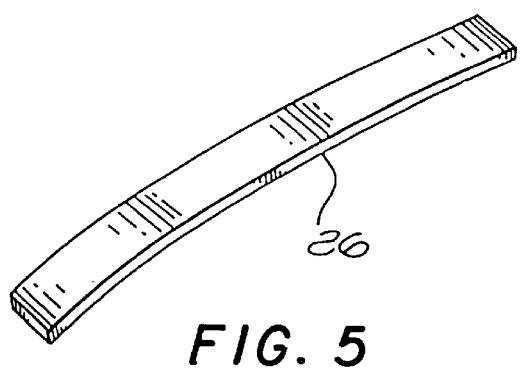
FIG. 5 is a perspective view of one embodiment of the strap of the present invention.

As shown in FIG. 5, one embodiment of the present invention is a strap that may be wrapped around a blood vessel to provide a snug fit, and then locked in place by any suitable means known in the art. Examples of suitable means are described in more detail below, but generally may including sewing, adhesives, melting using a cauterizing instrument or the like, hook and loop type fasteners, other bands or fasteners, snaps, belt buckles, friction type buckling systems, or other systems known in the art.

Figure 6:
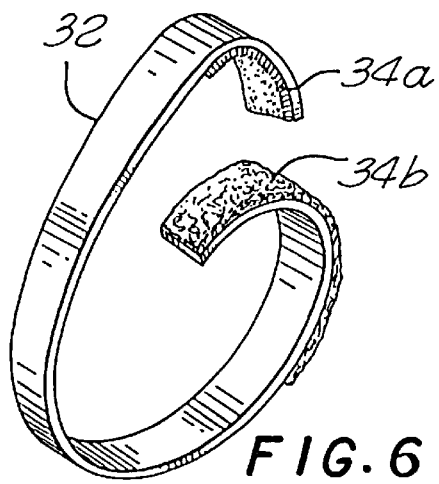
FIG. 6 is a perspective view of another embodiment of the present invention in a partially folded configuration.

As shown in FIG. 6, one embodiment of the present invention is disclosed in which the strap 32 is generally a flat strap with mating hook and loop type fastening means (Velcro®) disposed on opposite sides of the strap so that they mate when the strap is folded into a circular configuration, and are used to lock the strap around a blood vessel. The hook and loop system, depicted by numerals 34a and 34b, are sufficiently long and disposed along a sufficient length of the strap 32 that the strap will have the desired length when closed around a blood vessel to provide the desired snug fit.

Figure 7:
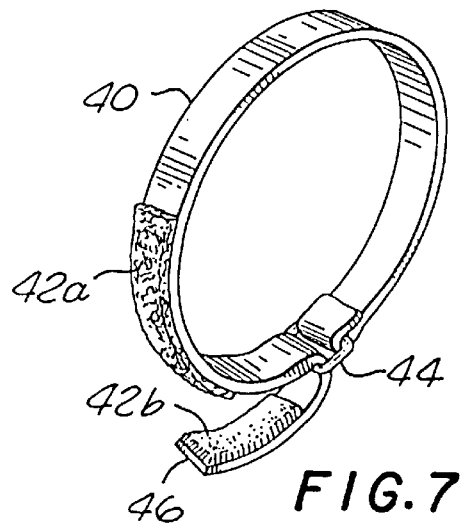
FIG. 7 is a perspective view of an alternative embodiment of the strap of the present invention.

As shown if FIG. 7, another embodiment of the present invention also utilizes a strap 40 with a hook and loop system, 42a and 42b disposed on the same side of the strap 40, and a buckle 44 through which end 46 of strap 40 is disposed, so that the strap 40 doubles back on itself and is locked in a closed circular configuration.

Figure 8:
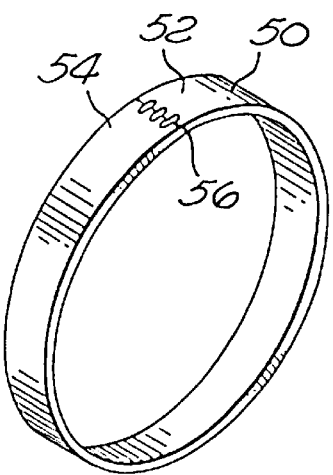
FIG. 8 is a perspective view of the another alternative embodiment of the strap of the present invention.

As shown in FIG. 8, in another embodiment of the present invention is a strap 50, similar to the form shown in FIG. 5, in which the ends 52 and 54 are sewn together with stitching 56.

Figure 9:
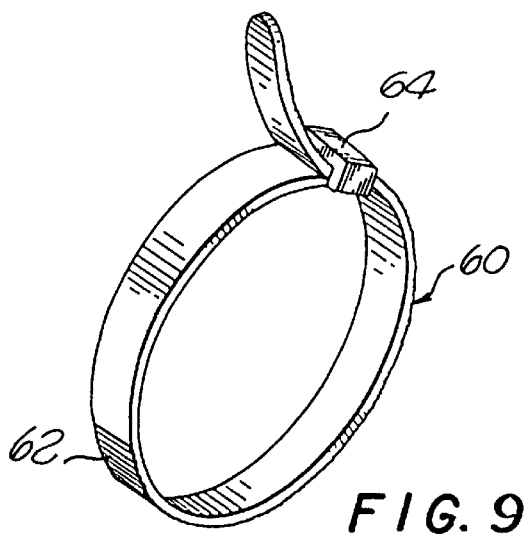
FIG. 9 is a perspective view of another alternative embodiment of the strap of the present invention.

As shown in FIG. 9, in another embodiment of the present invention is a strap 60 having a plurality of detents or ridges 62 on one surface and a buckle 64, like a cable tie buckle, which is known in the art, which locks the strap in a circular configuration when the end 66 is passed through the buckle 64 and pulled tight. This arrangement is advantageous because there are devices which can tighten such a strap to a desired tension, and such tensioning devices are already in use in medical, and particularly, surgical, applications. One example of such a tensioning device for these straps is a Panduit GS2B (Tinley Park, Ill.).

Figure 10:
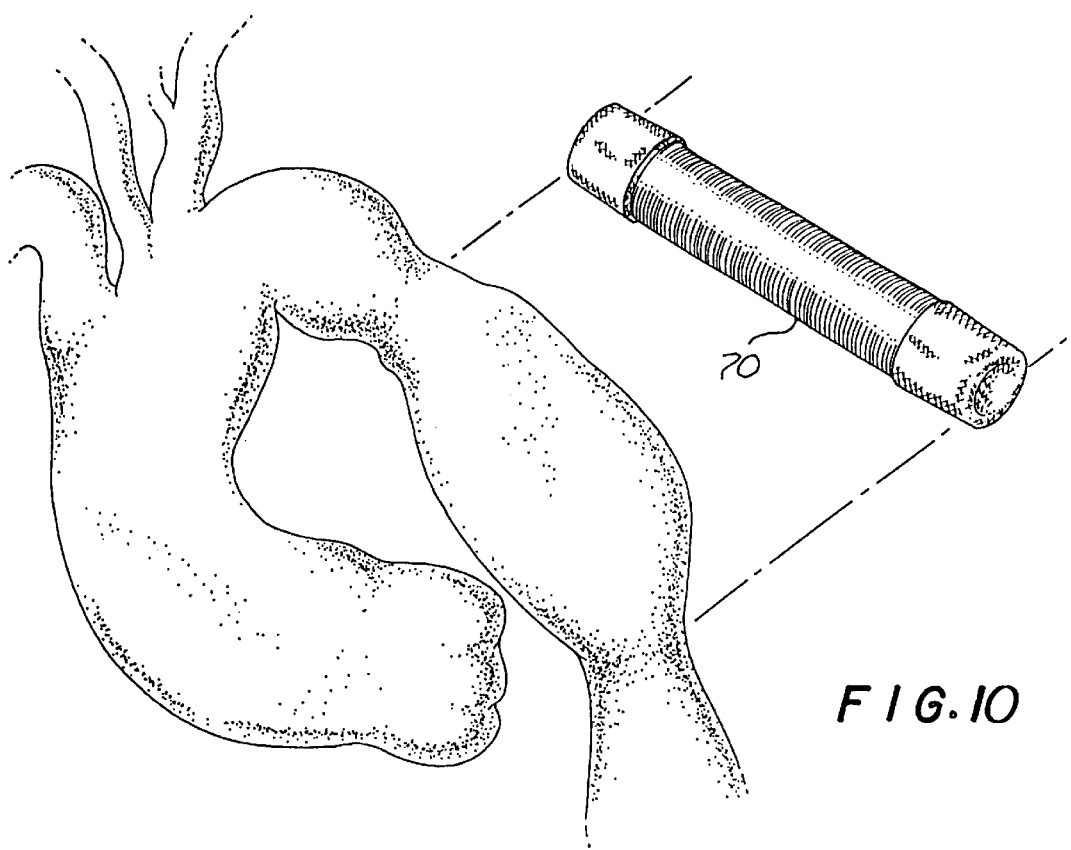
FIG. 10 is a perspective view of a prior art vascular graft.
Figure 11:
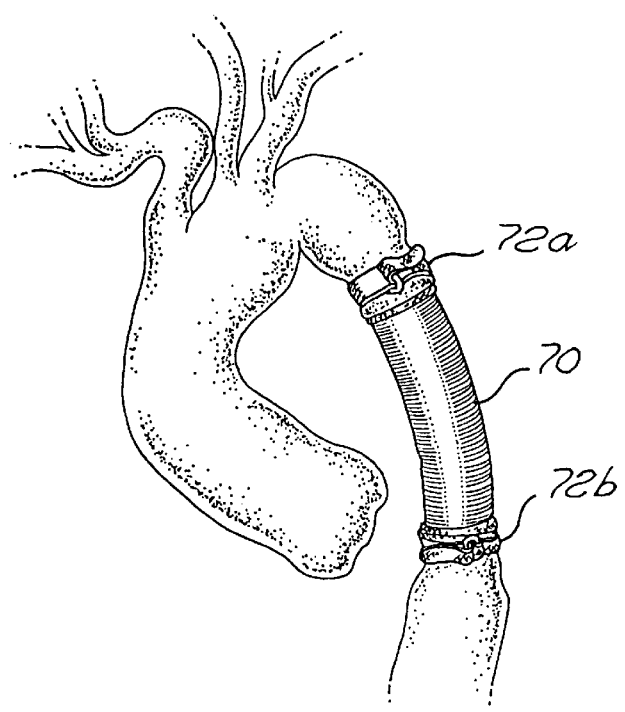
FIG. 11 is a perspective view of the present invention being used to retain a vascular graft.

As shown in FIGS. 10 and 11, the present invention can be used to secure an intraluminal vascular prosthesis or graft. A section of the aorta is shown with a dilated lumen as is known in the art. The graft 70, which is known in the art and can be obtained commercially from companies such as C. R. Bard, Inc., Vascular Systems Division, Billerica, Mass. The graft can be attached to the section of the aorta by means of the present invention 72a and 72b which is disposed within the walls of the lumen.

Figure 12:
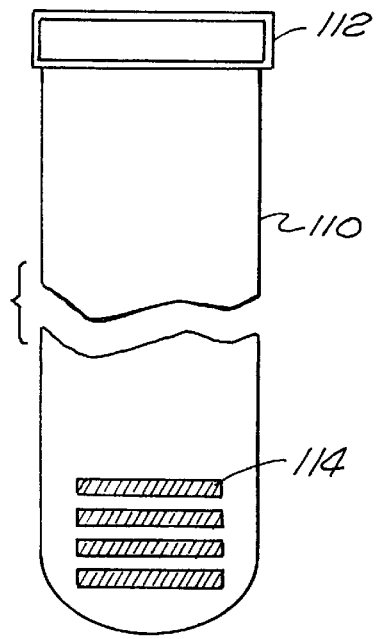
FIG. 12 is a planar top portion view of an embodiment of the strap of the invention wherein the strap contains a cable-tie buckle on one end and ridges on the other end.
Figure 13:
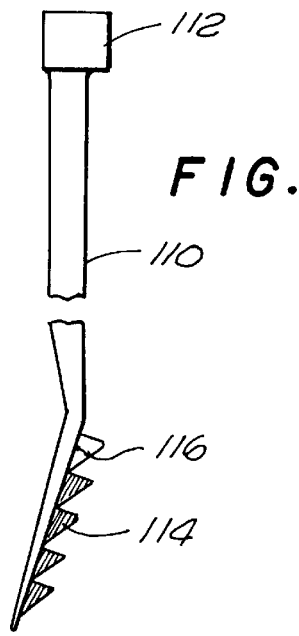
FIG. 13 is a side elevational view of the embodiment of the strap of the invention wherein the strap contains a cable-tie buckle on one end and ridges on the other end.
Figure 14:
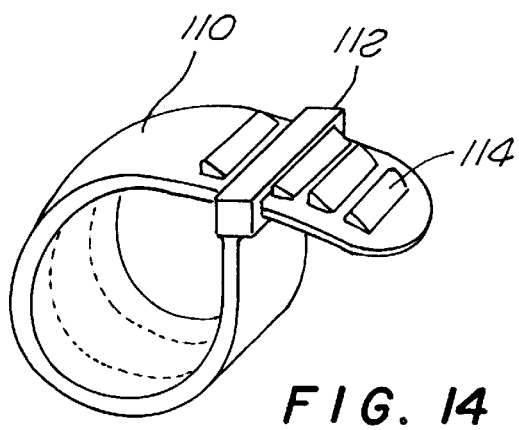
FIG. 14 is a perspective view of the embodiment of the strap of the invention wherein the strap contains a cable-tie buckle on one end and ridges on the other end, and wherein the end with the ridges is inserted into the cable-tie buckle.

FIGS. 12–14 presents an embodiment of the support strap 110 of the invention wherein the strap contains a cable-tie buckle 112 on one end and a plurality of ridges 114 on the other end. The fastening means of a cable-tie buckle is not new and is, in fact, well-known in areas outside the medical industry. The support strap 110 is secured around the blood vessel by forcibly inserting the end of the support strap 110 with the ridges 114 through the buckle 112 and using the force of the ridges 114 against the buckle 112 to hold the support strap 110 in place. As illustrated in FIG. 13, the protrusion of the ridges 114 is at an angle 116, approximately 100 to 600 relative to the support strap, so that the support strap 110 can be forcibly inserted into the cable-tie buckle 112 (primarily by deformation of the ridges 114) and the protruding ridges 114 retain and secure the support strap 110 within the buckle 112.

Figure 15:
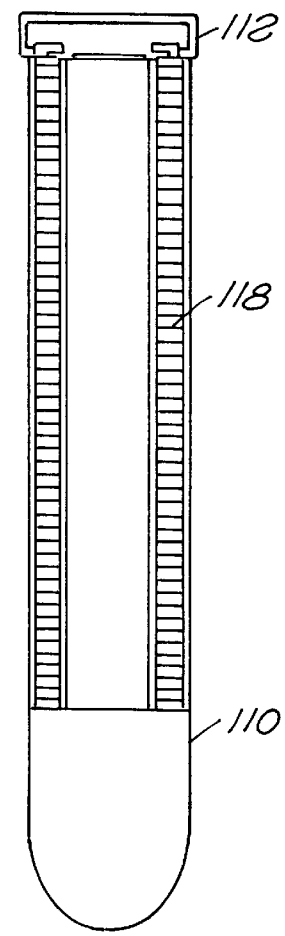
FIG. 15 is a planar bottom portion view of an embodiment of the invention wherein the bottom portion of the support strap contains a plurality of teeth to contact the blood vessel and provide additional gripping support to the strap against the blood vessel.

FIG. 15 presents a planar bottom portion view of an embodiment of the invention wherein the bottom portion of the support strap 110, or the portion that is in contact with the blood vessel, contains a plurality of teeth 118 on either side of the support strap 110 width. The teeth 118 contact the blood vessel and provide additional gripping support to the support strap 110 against the blood vessel. Either rigid or deformable teeth 118 can be used to provide additional support.

Figure 16:
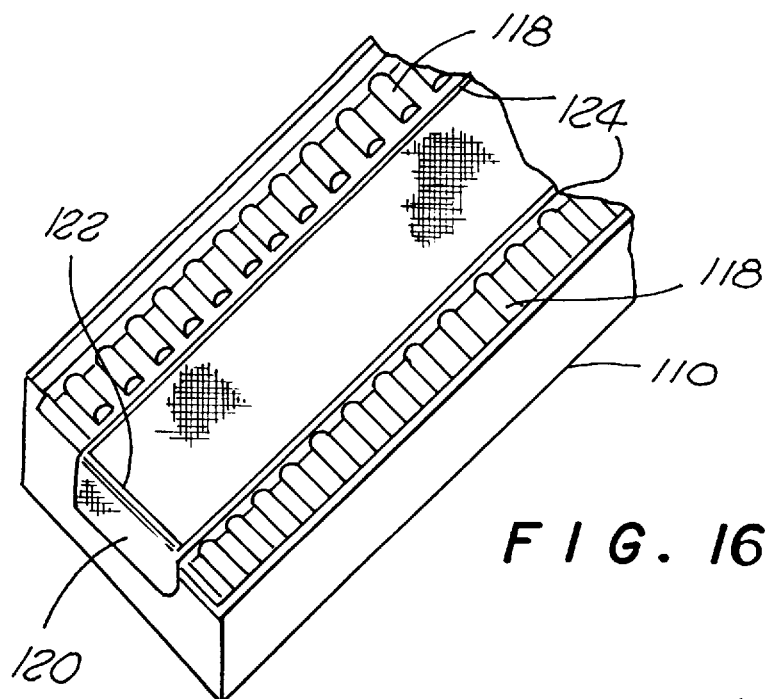
FIG. 16 illustrates a perspective cut-away view of an embodiment of the invention wherein the bottom portion of the support strap contains a plurality of teeth on either side of a channel to contact the blood vessel and provide additional gripping support to the strap against the blood vessel and wherein the channel is covered with a penetrable membrane.

In FIG. 16, the teeth 118 on either side of the bottom portion of the support strap 110 are separated by a shallow channel 120. In this embodiment, the channel 120 extends the length of the bottom portion of the support strap 110. The channel 120 is particularly useful for those applications wherein the graft retention system contains barbs or stables that penetrate the blood vessel wall. The invention contemplates that the support strap wraps around the blood vessel and covers the exposed barbs or staples. Because the barbs or staples are exposed, or extend through the exterior walls of the blood vessel, the support strap cannot directly contact the exterior wall of the blood vessel where the barbs or staples are located. By including a channel 120 in the strap, the exposed portion of the barbs or staples on the outside of the blood vessel penetrate into the channel 120 of the support strap 110, the barbs or staples do not inhibit direct contact between the support strap 110 and the exterior wall of the blood vessel. In other words, the channel 120 provides additional area for the exposed barbs or staples to extend into, while the sides of the support strap 110 can contact the wall of the blood vessel without being displaced by the barbs or staples. Thus, the inclusion of the channel 120 permits the support strap 110 to contact the blood vessel more completely and more uniformly.

FIG. 16 also demonstrates a further embodiment of the invention wherein the channel 120 of the support strap 110 is covered with a penetrable support membrane 122 that the exposed barbs or staples must further penetrate to enter the channel 120. When punctured by the exposed barbs or staples, the penetrable support membrane 122 provides additional gripping support to the support strap 110 by retaining the exposed barb or staple at the point where the barb or staple enters the channel 120.

Each side of the channel 120 in FIG. 16 is lined with radio-opaque markings 124 that serve to identify the location of the channel 120. An identification of the location of the channel 120 in the support strap 110 permits the surgeon to effectively position the exposed barbs or staples into the channel 120. The preferred embodiment utilizes radio-opaque markings 124 on either side of the channel 120. The invention contemplates, however, that any surgically compatible markings sufficient to indicate to the surgeon the location of the channel may be employed.

Figure 17:
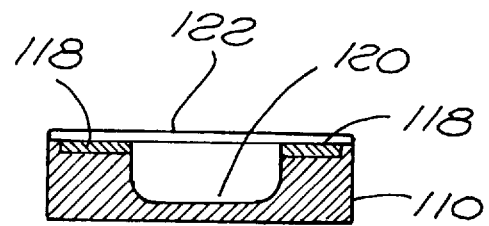
FIG. 17 illustrates a side elevational view of an embodiment of the invention wherein the bottom portion of the support strap contains a plurality of teeth on either side of a channel to contact the blood vessel and provide additional gripping support to the strap against the blood vessel and wherein the channel is covered with a penetrable membrane.
Figure 18:
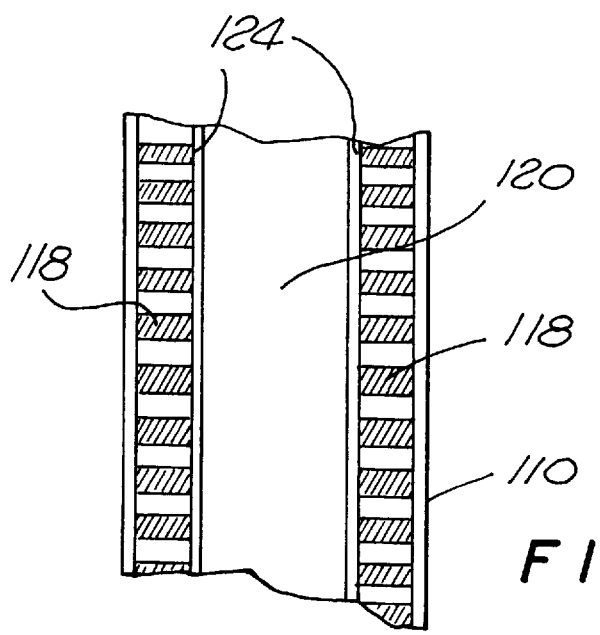
FIG. 18 illustrates a planar bottom portion cut-away view of an embodiment of the invention wherein the bottom portion of the support strap contains a plurality of teeth on either side of a channel and radio-opaque markings to mark the channel and assist the surgeon of the location of exposed barbs or staples into the channel.

FIG. 17 illustrates a side elevational view of the support strap 110. The bottom portion of the support strap 110 in FIG. 17 includes a plurality of teeth 118 separated by a shallow channel 120. The shallow channel 120 is covered with a penetrable support membrane 122. FIG. 18 presents a planar view of a cut-away portion of the bottom portion of the support strap 110, including a plurality of teeth 118 separated by a shallow channel 120. On either side of the channel 120 are radio-opaque markings 124 that serve to identify the location of the channel 120.

Figure 19:
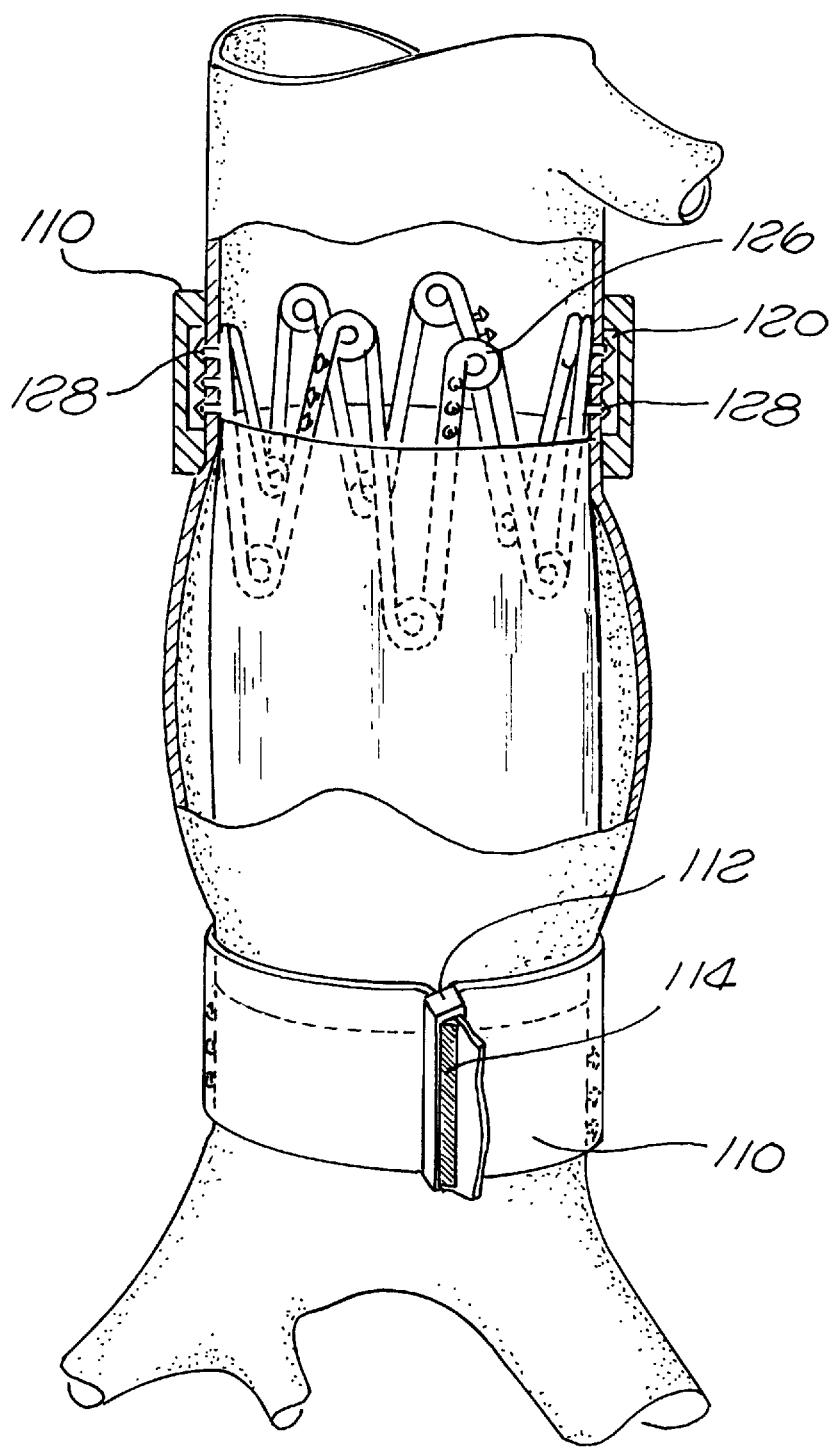
FIG. 19 illustrates a partial sectional view of an aneurysmal blood vessel with a vascular graft disposed therein, and the bands of the invention that are support straps with shallow channels on the bottom portion of each support strap, wherein the support straps are disposed around the blood vessel at the sites where the retention system engages the blood vessel, and wherein exposed portions of the graft retention system are located in the shallow channels in the support straps.

FIG. 19 illustrates a partial sectional view of an aneurysmal blood vessel with a vascular graft inside the blood vessel. The vascular graft is secured to the blood vessel by a graft retention system 126 that includes barbs or staples 128 that penetrate through the blood vessel. The aneurysmal blood vessel is surrounded by a band that is a support strap at the site where the barbs or staples 128 engage the blood vessel. The support strap has a closure means that is a cable-tie buckle 112 through which a strap end with protruding ridges 114 is inserted and held in place. In FIG. 19, the support strap 110 includes a channel 120 extending the length of the bottom portion of the support strap 110. The exposed portion of the barbs or staples 128 penetrate into the channel 120 of the support strap 110. Thus, FIG. 19 illustrates that the barbs or staples 128 do not inhibit direct contact between the support strap 110 and the exterior wall of the blood vessel, because the barbs or staples 128 are located in the channel 120.

Many of the support straps or bands described above and contemplated by the invention include closure means that are attached directly to the end or ends of the band or support strap. Examples of this type of closure means include the hook and loop type fasteners as well as the cable-tie buckle. These bands or support straps can be tightened and retained easily by pulling the band or strap through the closure means. The invention also contemplates types of closure means that are not attached to or are part of the band itself. Examples of this type of closure means include sutures or clamps that are added to the band or strap after the band or strap is wrapped around the blood vessel.

Figure 20:
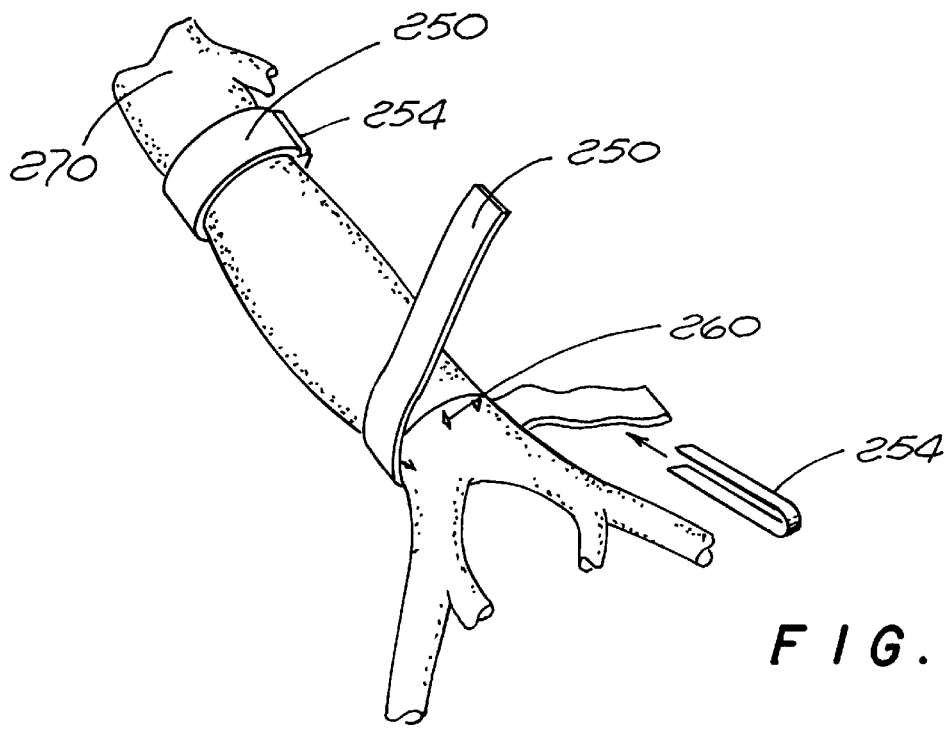
FIG. 20 is a perspective view of an artery with an aortic graft assembly in place, one material band in place, and a second material band partially around the outside of the artery at a site where the graft retention system attaches to the artery.

FIG. 20 illustrates a graft retention band 250 of this latter type which is secured in place by a separate clip 254. Clip 254 is similar to a barrette clip for hair and is crimped onto the ends of band 250 to secure it in place. As shown in FIG. 20, a damaged blood vessel 270 has a graft assembly inserted therein and held in place by a graft retention system, a portion of which is seen at 260. This graft retention system may be the same as those previously described, but the invention is not limited in this regard. A pair of material bands 250 are wrapped around the damaged blood vessel 270 at each end of the graft.

Figure 21:
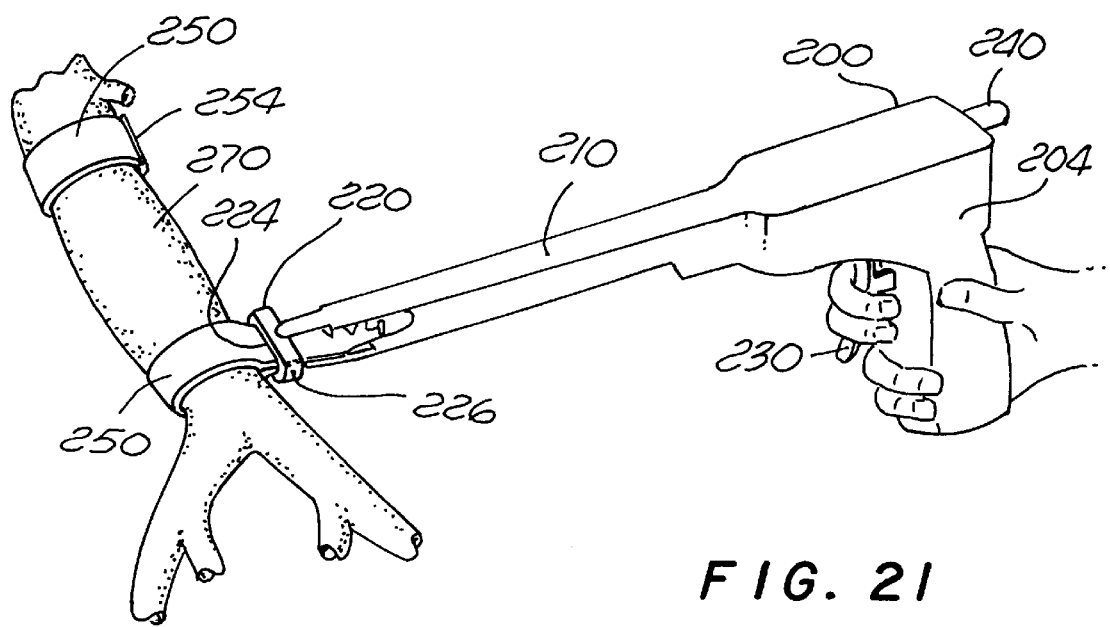
FIG. 21 is a perspective view of the strap gun device that is used to secure a material band on a blood vessel.

It will be observed that the use of a separate clip 254 to secure the ends of bands 250 would present a challenging task using only conventional surgical tools. Accordingly, a special tool 200 is provided for securing bands 250 as illustrated in FIG. 21. The significant components of tool 200 include a handle 204, a shaft 210, and a crimping and cutting head 220. Clip 254 is loaded into head 220 through side slot 226. The tool also contains gripping and tightening mechanisms that are actuated by trigger 230. Trigger 230 also controls the operation of the crimping and cutting head 220 as will be more fully explained below. During the surgical procedure, after the surgeon has wrapped material band 250 around blood vessel 270, both ends of the material band are loaded into tool 200 through slot 224 in crimping and cutting head 220. As will be described below, the two ends of the band are fed through the device until they are placed under a gripping cam. Actuation of trigger 230 engages the cam against the ends of the band and pulls it around blood vessel 270 until a predetermined tension is reached. At that point, clip 254 is crimped onto the ends of band 250 and the excess band material is cut off.

Figure 22:
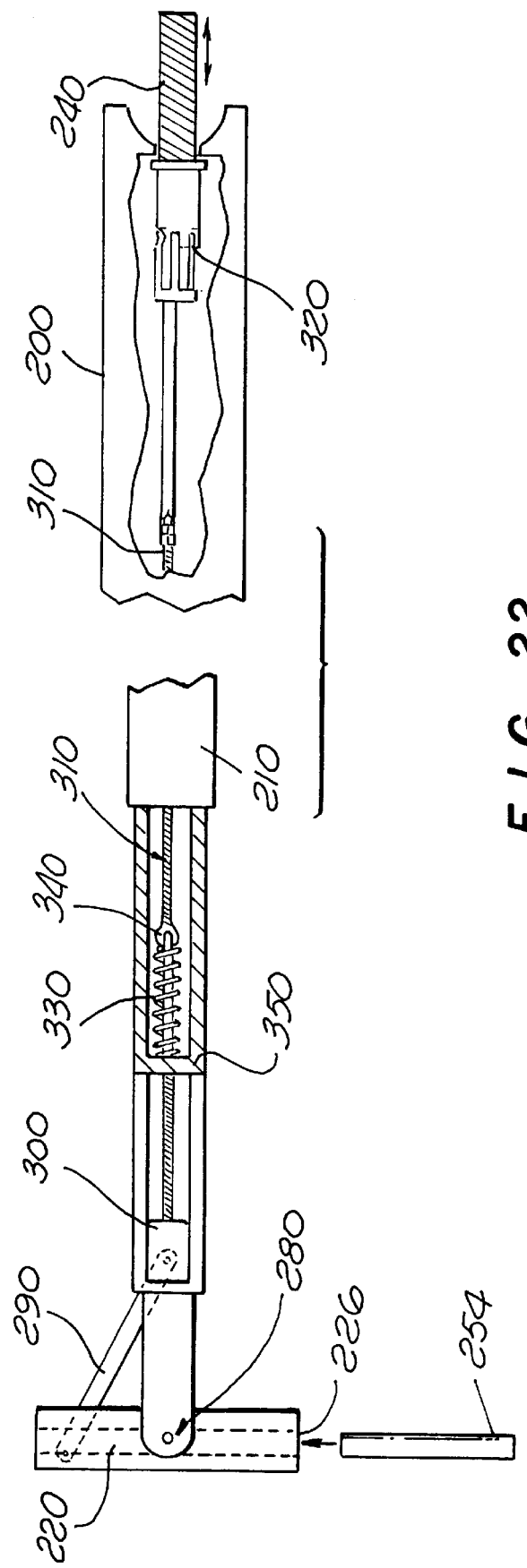
FIG. 22 is a partially cut-away view of the strap gun illustrating operation of the crimping and cutting head.

Referring now to FIG. 22, a partially cut-away view of tool 200 is shown. As generally indicated in FIG. 21, the ends of band 250 are inserted through slot 224 of the crimping and cutting head 220. It is desirable that band 250 have a width in the range of approximately 2.0 to 2.5 cm. However, to avoid unnecessary trauma to the patient, it is desirable to have the portion of tool 200 that is to be inserted into the patient fit within a tube that is no larger than about 10–12 mm in diameter. To accomplish this objective while still accommodating the desired width of band 250, the crimping and cutting head 220 pivots at the end of shaft 210 so as to align with the shaft while the tool is inserted to the site of the arterial repair.

Crimping and cutting head 220 is attached to the end of shaft 210 at pivot 280. Pivotal motion of head 220 is effectuated by arm 290, which is pivotally coupled at one end to head 220. The other end of arm 290 is pivotally coupled to sliding member 300, which slides axially within shaft 210. Axial movement of sliding member 300 is controlled by button 240 at the handle end of tool 200. The mechanism for rotating head 220 between its operating position as shown in FIG. 21 and its retracted position aligned with shaft 210 is similar to that of a conventional "click-type" ball-point pen. Button 240 is coupled to actuating rod 310 through ratchet assembly 320. A spring 330 is compressed between boss 340 on rod 310 and stationary wall 350 of shaft 210. Thus, by repeatedly pushing button 240, head 220 is alternately moved between its operating and retracted positions.

Figure 23:
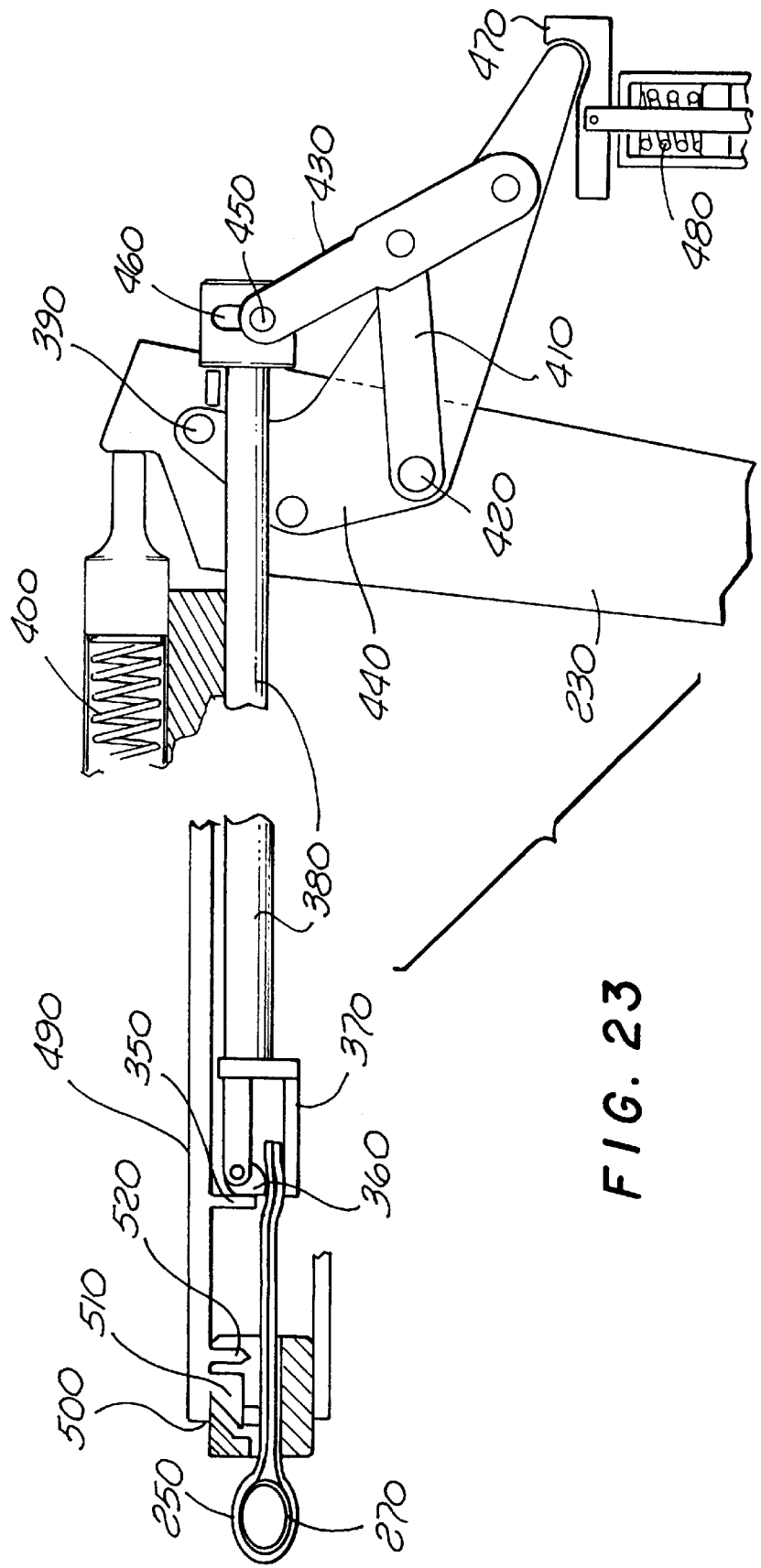
FIG. 23 is a partially cut-away view of the strap gun with the trigger released.

Referring now to FIG. 23, the mechanism for tightening band 250 will be described. As indicated earlier, the ends of band 250 are inserted through receiving slot 224 in head 220 which already contains clip 254. The ends of band 250 are guided between cam 360 and holding plate 370. Cam 360 and holding plate 370 are both coupled to slider 380, which is actuated by trigger 230 as described below. Cam 360 is spring-biased in a downward direction to clamp the ends of band 250 against holding plate 370. However, in the forward position of slider 380 illustrated in FIG. 23, cam 360 is held in an open position against wall 214 of shaft 210.

Figure 24:
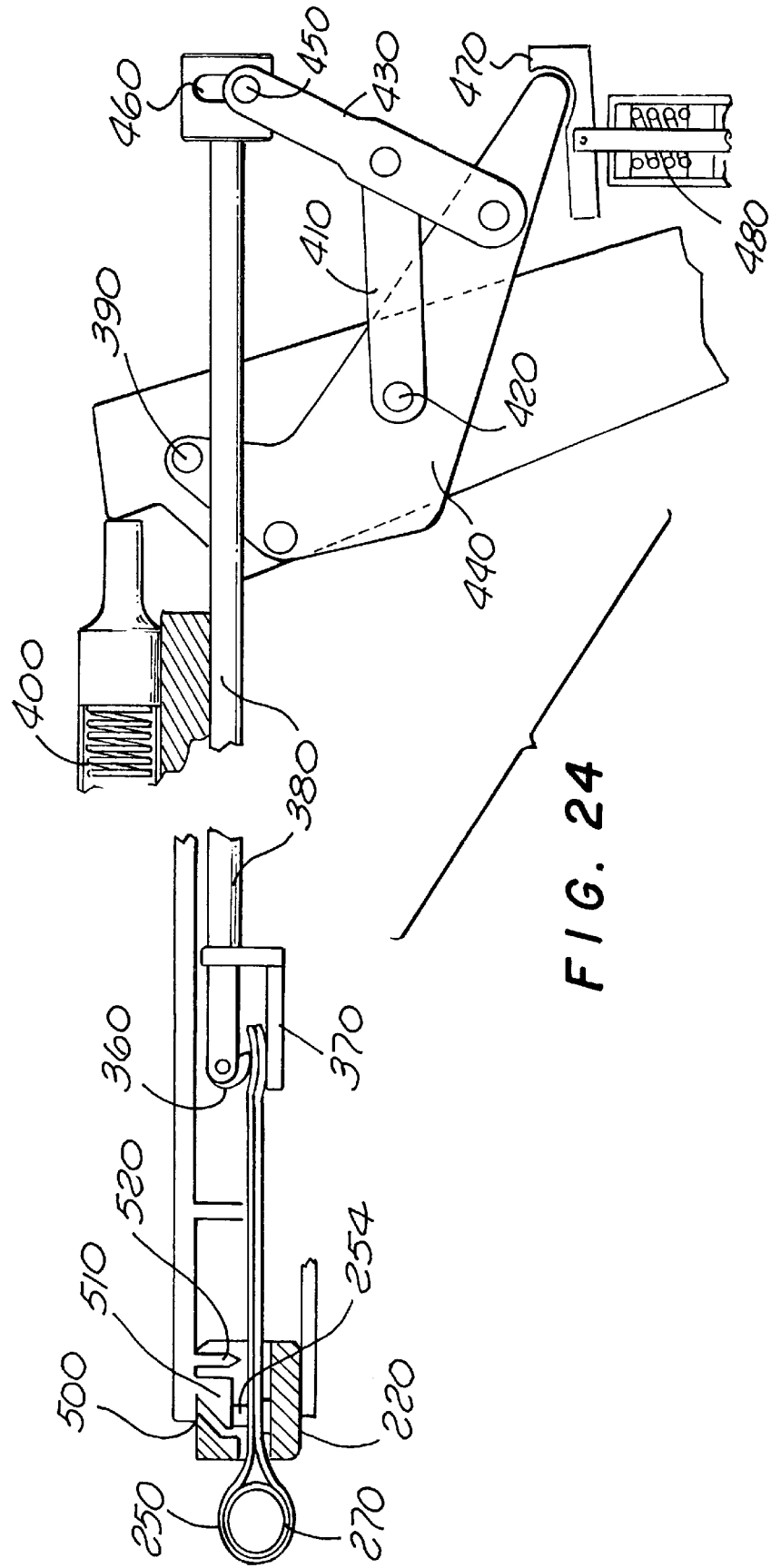
FIG. 24 is a partially cut-away view of the strap gun with the trigger actuated to tension the material band.

With reference now to FIG. 24, slider 380 is shown in its retracted position wherein cam 360 has engaged the ends of strap 250 against holding plate 370. As mentioned, the actuation of slider 380 is controlled by trigger 230, which pivots about axis 390. Trigger 230 is biased toward its forward position by spring 400. Connecting arm 410 is pivotally coupled to trigger 230 at pivot axis 420. Connecting arm 410 is also pivotally connected to rocker arm 430, which is pivotally coupled at its lower end to tension arm 440. The upper end of rocker arm 430 is coupled to slider 380 at pivot 450, which slides vertically in slot 460. Tension arm 440 pivots on the frame of tool 200 at trigger axis 390 and is also located by retainer 470. As trigger 230 is pulled rearwardly from the position shown in FIG. 23 towards the position shown in FIG. 24, rocker arm 430 pivots on tension arm 440 and retracts slider 380. The total travel of slider 380 is approximately 3 cm.

Retainer 470 is held in position by tension spring 480. As band 250 is tensioned by the retraction of slider 380, tension spring 480 begins to compress, thereby allowing tension arm 440 to pivot downwardly on axis 390. Tension arm 440 is coupled to blade lever 490, which is coupled to crimping and cutting head 220 at pivot axis 500. As blade lever 490 is pivoted in a downward direction by tension arm 440, bar 510 first contacts clip 254 and crimps it in place against the ends of bands 250 and then blade 520 cuts off the loose ends of band 250. Once clip 254 is crimped in place, it can be withdrawn through slot 224 and head 220 can then be returned to its stowed position in which it is axially aligned with shaft 210.

While the method and apparatus have been described in terms of various embodiments, other embodiments may come to mind to those skilled in the art without departing from the spirit and scope of the present invention. The invention should, therefore, be measured in terms of the claims which follow.

What I claim is:

1. In a vascular graft for resolving an aneurysm in a blood vessel of the type comprising a generally liquid impervious, tubular, collapsible, and expandable body having a first and second end, and a graft retention system disposed at each of said first and second ends for retaining said graft in a blood vessel, in use, said graft retention system being collapsible and expandable, the improvement comprising a support strap adapted to surround the exterior of said blood vessel, said support strap having a closure means for retaining said strap in a circular configuration when said strap is disposed around a blood vessel at a location adjacent to each of said graft retention systems, and said support strap further having a plurality of teeth on a length of said strap.

2. In a vascular graft for resolving an aneurysm in a blood vessel of the type comprising a generally liquid impervious, tubular, collapsible, and expandable body having a first and second end, and a graft retention system disposed at each of said first and second ends for retaining said graft in a blood vessel, in use, said graft retention system being collapsible and expandable, the improvement comprising a support strap adapted to surround the exterior of said blood vessel, said support strap having a closure means for retaining said strap in a circular configuration when said strap is disposed around a blood vessel at a location adjacent to each of said graft retention systems, wherein said closure means comprises a cable-tie buckle at one end of said support strap and protruding ridges on a side of said support strap wherein said protruding ridges secure said support strap within said cable-tie buckle.

3. In a vascular graft for resolving an aneurysm in a blood vessel of the type comprising a generally liquid impervious, tubular, collapsible, and expandable body having a first and second end, and a graft retention system disposed at each of said first and second ends for retaining said graft in a blood vessel, in use, said graft retention system being collapsible and expandable, the improvement comprising a support strap adapted to surround the exterior of said blood vessel, said support strap having a closure means for retaining said strap in a circular configuration when said strap is disposed around a blood vessel at a location adjacent to each of said graft retention systems, said support strap further having a channel along the length of said strap.

4. The support strap of claim 3, wherein said support strap includes a penetrable membrane coupled to said support strap and covering said channel.

5. The support strap of claim 4, wherein said support strap includes a marking to indicate the location of said channel.

6. The support strap of claim 5, wherein said marking is a radio-opaque marking.

* * * * *